Figure 1:
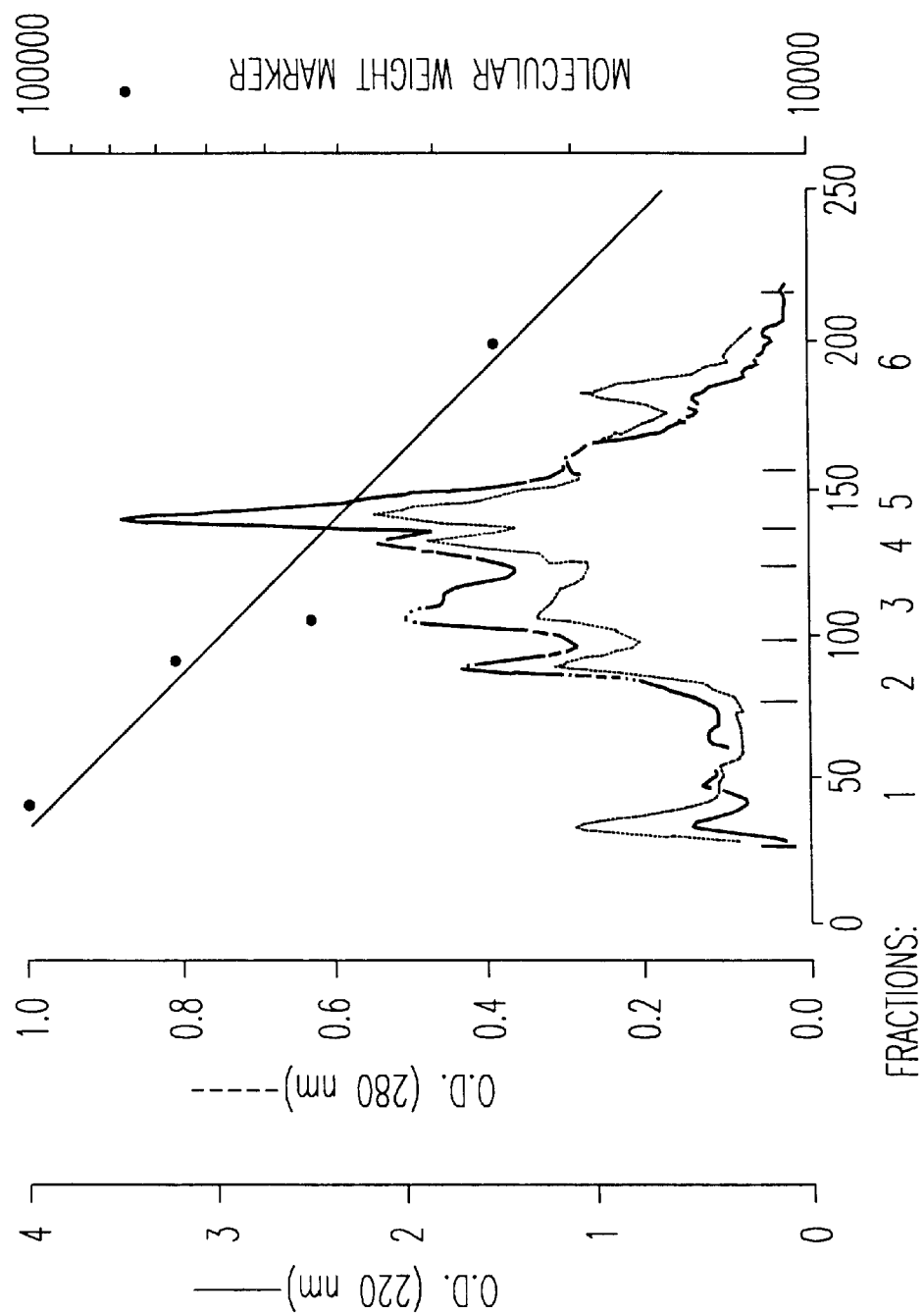

United States Patent [19]
Marchal et al.

[11] Patent Number: 6,060,259
[45] Date of Patent: *May 9, 2000

[54] MYCOBACTERIUM PROTEINS AND APPLICATIONS

[75] Inventors: Gilles Marchal, Ivry; Felix Romain, Fontenay-Les-Briis; Pascale Pescher; Cynthia Horn, both of Paris, all of France

[73] Assignee: Institut Pasteur, Paris Cedex, France

[ * ] Notice: This patent is subject to a terminal disclaimer.

[21] Appl. No.: 08/351,134

[22] Filed: Nov. 30, 1994

Related U.S. Application Data

[63] Continuation-in-part of application No. PCT/FR92/00508, Jun. 5, 1992.

[30] Foreign Application Priority Data

Jun. 7, 1991 [FR] France ................................. 91 06970

[51] Int. Cl.⁷ ................................................ G01N 33/554
[52] U.S. Cl. ..................... 435/7.32; 530/350; 424/200.1; 424/203.1; 424/248.1
[58] Field of Search .......................... 435/7.32; 530/350; 424/248.1, 200.1, 203.1

[56] References Cited

U.S. PATENT DOCUMENTS 5,599,541  2/1997  Marchal et al. ...................... 424/190.1

FOREIGN PATENT DOCUMENTS

WO 89/09261  10/1989  WIPO .
9221758      4/1996   WIPO .

OTHER PUBLICATIONS

Fifis et al. Infect. & Immun. Mar. 1991. 59(3):800–807.
DeBruyn et al. Infect. & Immun. 1987.55(1):242–252.
Romain et al. Feb. 1993. Infection & Immunity 61(2):742–750.
Carlin et al. Aug. 1992. Infection & Immunity 60(8): 3136–3142.
International Preliminary Examination Report for PCT/FR 92/00508 Dated Aug. 27, 1993 with English Translation.
International Preliminary Examination Report for PCT/FR 92/00508 Dated Apr. 7, 1993.
International Search for PCT/FR 92/00508 Dated Sep. 11, 1992.
Search Report for FR 9106970 dated Jan. 23, 1992.
Miura et al, "Comparative Studies with Various Substrains of Mycobacterium Bovis BCG on the Production of an Antigenic Protein, MPB70", *Infection and Immunity*, vol. 39, (1983), pp. 540–545.
Abou–Zeid et al, "Characterization of the Secreted Antigens of Mycobacterium Bovis BCG: Comparison of the 46–Kilodalton Dimeric Protein with Proteins MPB64 and MPB70", *Infection and Immunity*, vol. 55, (1987), pp 3213–324.

*Primary Examiner*—James C. Housel
*Assistant Examiner*—Jennifer Graser
*Attorney, Agent, or Firm*—Oblon, Spivak, McClelland, Maier & Neustadt, P.C.

[57] ABSTRACT

Mycobacterium proteins, in particular those of *M. bovis*, having molecular weights between approximately 44.5 and 47.5 kD. These proteins can have molecular weights of approximately 45 kD or 47 kD and isoelectric pH of approximately 3.7 (45 and 47 kD proteins) and 3.9 (47 kD proteins).

These proteins or hybrid proteins containing a part of their sequences can be used as vaccines or as drugs, or for the detection and monitoring of tuberculosis in particular in man and in cattle.

11 Claims, 11 Drawing Sheets

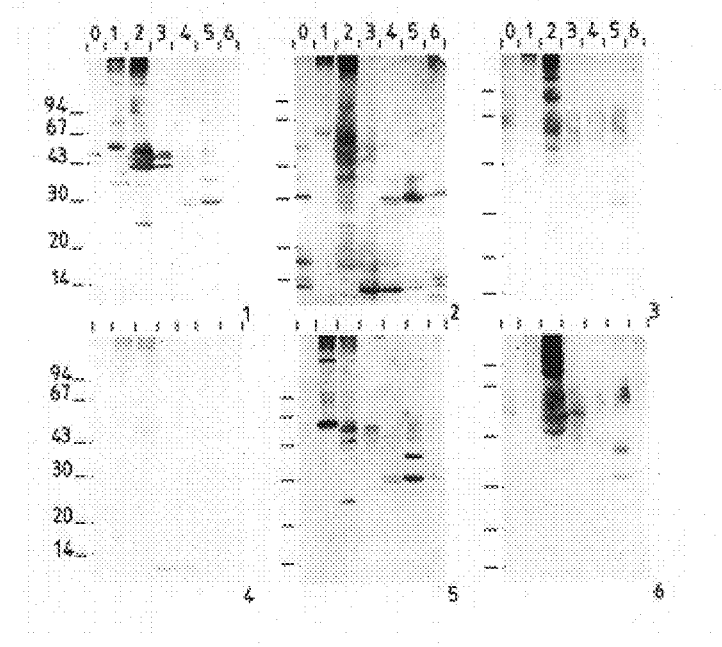
FIG.7A-F
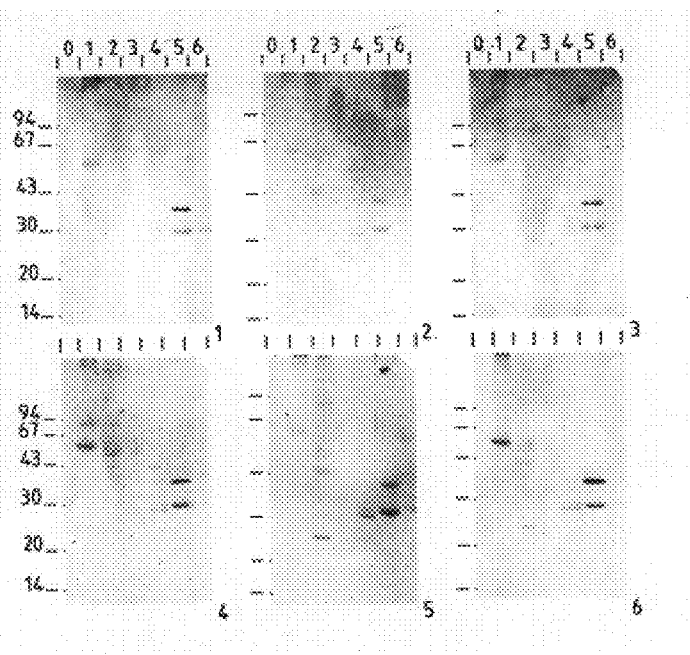
FIG.7G-L

MYCOBACTERIUM PROTEINS AND APPLICATIONS

This is a continuation-in-part application of International Patent Application PCT/FR 92/00508, filed on Jun. 5, 1992.

The present invention relates to Mycobacterium proteins, in particular those of M. bovis, having molecular weights between approximately 44.5 and 47.5 kD and the nucleotide sequences coding for these proteins.

The present invention also relates to those protein fractions obtained from cultures of Mycobacterium bovis, showing a specific immunological reactivity towards anti-tuberculosis antibodies.

It also relates to the use of these proteins and fractions for the detection and monitoring of tuberculosis and as vaccines.

Tuberculosis continues to be a public health problem throughout the world. The annual number of deaths directly related to tuberculosis is around 3 million and the number of new cases of tuberculosis is around 15 million. This number of deaths due to tuberculosis is high even for the developed countries; for example in France it is of the order of 1500 per year, a figure which is certainly underestimated by a factor of 2 or 3 if Roujeau's assessments of the differences between official figures and the results of systematic autopsies are taken into account. The recent increase in tuberculosis cases, or at least the leveling-off of the decrease in the frequency of this disease, must be considered in correlation with the development of the HIV/AIDS epidemic. In total tuberculosis remains the leading infectious disease in terms of frequency in France and the developed countries, but above all in the developing countries for which it constitutes the principal source of human loss related to a single disease.

At present, a definite diagnosis made by the demonstration of cultivable bacilli in a sample taken from the patient is only obtained in less than half the cases of tuberculosis. Even for pulmonary tuberculosis, which represents 80 to 90% of the tuberculosis cases, and which is the form of the disease for which the detection of the bacilli is the easiest, the examination of sputum is only positive for less than half the cases.

The development of the most sensitive techniques such as PCR (Polymerized Chain Reaction), always comes up against the necessity for obtaining a sample. Since women and children do not habitually spit, sampling for infants frequently requires specialized medical intervention (for example ganglionic biopsy or sampling by lumbar puncture of the cephalo-rachidian fluid).

In other respects, inhibitions of the PCR reaction itself exist, of a type such that a sample can be unusable by this technique because of the impossibility of controlling their origins.

Finally, the conventional bacteriological diagnosis, microscopic examination and culture, because of its sensitivity limits (at the best of the order of $10^4$ to $10^5$ bacilli in the sample) requires that there has already been a relatively substantial development of bacilli and thus of the disease.

The detection of specific antibodies directed against Mycobacrerium tuberculosis should thus be of assistance in the diagnosis of the common forms of the disease for which the detection of the bacilli themselves is difficult or impossible.

Successive generations of research workers have attempted to perfect a serological diagnosis technique for tuberculosis. From Ardoing (C.r. hebd. Seanc. Acad. Sci. Paris; 1898: 126: 1398–1401) to Middlebrook and Dubos (J. Exp. Med. 1948, 88: 521–528), the preparations used for this diagnosis have been very little or not purified, the effort being directed above all towards an increase in sensitivity and not specificity. Recently again techniques tending to increase only the sensitivity have been suggested using a technique of either the ELISA or RIA type.

The more recent work of Daniel and Janicki (*Microbiol. Rev.* 1978, 42; 84–113) or Wiker et al. (*Scand. J. Immunol.* 1988, 27: 223–239) has shown the complexity of the mycobacterial antigens. Following this work, attempts have been made to define the principal antigens able to be used for diagnostic purposes (Chan et al., *Am. Rev. Respir. Dis.* 1990, 142: 385–390). A serological test has as a result been commercially available (ANDA) for 3 or 4 years. It uses an extremely complex antigen, poorly characterized biochemically, the A60 of Cocito and Vanlinden (*Clin. Exp. Immunol.* 1986, 66: 262–272). The specificity and sensitivity of this test are poor. It is not of great help in diagnosis and has been highly criticized if not rejected by numerous biologists who have used it widely.

Well characterized antigens, corresponding to quantitatively abundant proteins, have also been tested for their specificity and sensitivity for serological diagnosis.

The α antigen of approximately 35 kD was first purified in 1965; it represents 25 to 35% of the proteins present in the culture medium of numerous strains of *M. tuberculosis, M. kansasii* or BCG (Fukui et al. Biken J. 1965, 8: 189–199).

An antigen of 64 kD has also been purified, representing more than 50% of the culture medium proteins, when these are grown in the absence of zinc (De Bruyn et al. *J. Gen. Microbiol.* 1981, 124: 353–357).

A second molecule has also been purified, representing 25 to 30% of the proteins in the same media. This molecule of 32 kD is very similar to the a antigen already described, but is nevertheless different (De Bruyn et al. *Microbiol. Pathogenesis* 1987, 2: 351–366).

Similarly, a molecule of 16 kD has been purified, and its presence has been observed in the culture medium of certain BCG (NCG Tokyo) and *M. bovis* strains and its absence or low level for other strains (BCG Copenhague, Pasteur) (Harboe and Nagai, *Am. Rev. Respir. Dis.* 1984, 139: 444–452).

The selection criteria for the proteins used by these authors have thus been in the first place biochemical criteria. The proteins have only been subsequently tested for their capacity to detect infection by tuberculosis.

Representative results of this approach thus show that the antibody response directed against the 64 kD thermal shock protein of mycobacteria is high in 80% of patients affected by tuberculosis, but also in 30% of infants affected by whooping cough (Thole et al. *Infect. Immun.* 1987, 55: 1466–1475).

The use of molecular biological techniques for gene cloning where the product is recognized by a polyclonal antibody of restricted specificity or a monoclonal antibody, has led to more or less the same results. In this case, the antibodies which have been used as probes, have been prepared against the antigens present in bacterial extracts or on killed bacteria. These extracts or bacteria having been as a general rule injected into Balb/C mice, the repertory of responses obtained is limited to the response of the mouse of this single cloning line, submitted moreover to extremely similar experimental protocols.

Having thus been recognized by certain monoclonal antibodies, such as the 65 kD or the 32 kD, the molecules have already been purified or are in the course of purification by a classical biochemical approach.

New molecules such as the 70 kD or 19 kD have also been detected by this technique. But when used for detection purposes, these molecules do not allow unambiguous distinction between patients affected by tuberculosis and normal subjects or those with other infectious diseases.

In recent work the purification of mycobacterial antigens has been attempted using a mixture of serums from tuberculosis patients to make an immuno-adsorbent allowing partial purification of the principal antigens recognized by the patients (Thongkrajai et al. *J. Med. Microbiol.* 1989, 30: 101–104).

The techniques reported in the prior art are thus mostly based on the preliminary isolation of proteins through their biochemical properties. It is not until after this isolation that the authors have tested the capacity of these proteins to detect those individuals affected by tuberculosis.

In the work leading up to the present invention, another method has been chosen to select the antigens representative of tuberculosis infection.

According to the invention, the work has been directed towards the unambiguous selection of the antigens representative of tubercular infection by the use of serums originating from patients affected by tuberculosis or from guinea pigs immunized with live bacilli.

This method, which is distinguished from those experiments described in the prior art, has allowed the isolation of antigens representative of tuberculosis, permitting the unambiguous detection of patients affected by this disease.

The present invention thus relates to the proteins of Mycobacterium and in particular of *M. bovis* having a molecular weight of between approximately 44.5 and 47.5 kD. These proteins can have molecular weights of approximately 45 kD or approximately 47 kD, within limits of error of ±10%, and isoelectric pH (pHi) of approximately 3.7 (proteins 45 and 45 kD) and 3.9 (proteins of 47 kD), with pHi limits of error of ±0.2.

The 10% error in the molecular weight determination is in particular due to variations in results according to the determination kit used (LMW Electrophoresis Calibration Kit, Ref. 17-0446-01, Pharmacia).

These proteins can also possess an amino-acid composition expressed by frequency for PRO of approximately 21.9%, for ASN/ASP approximately 10.6%, for THR approximately 5.4%, for SER approximately 5%, for GLN/GLU approximately 6%, for GLY approximately 7.4%, for ALA approximately 19.2%, for VAL approximately 5.8%, for ILE approximately 2.3%, for LEU approximately 4.7%, for TYR approximately 2.2%, for PHE approximately 2.2%, for LYS approximately 2.9%, and/or for ARG approximately 2.5%.

The 47 kD protein species can have an $NH_2$ terminal with the following sequence (SEQ ID N°1):

```
ALA-PRO-GLU-PRO-ALA-PRO-PRO-VAL-PRO-PRO-ALA-ALA-
 1   2   3   4   5   6   7   8   9   10  11  12

ALA-ALA-PRO-PRO-ALA
 13  14  15  16  17
```

The present invention also relates to a hybridoma line deposited on the Apr. 12, 1991 under the N°I-1081 as part of the Collection Nationale de Culture des Microorganismes (CNCM) of the Institut Pasteur, and to a hybridoma line deposited on Oct. 12, 1994 under the N°I-1483 as a part of the CNCM, and the antibodies secreted by these lines.

The proteins described above also have the property of being recognized by antibodies present in the serum of patients affected by tuberculosis or of animals able to be affected by tuberculosis, by certain antibodies obtained by immunization of guinea pigs with live *M. bovis bacilli*, or by an antibody secreted by the aforementioned hydridoma lines N°I-1081 or I-1483 and of not being recognized by antibodies obtained by immunization of guinea pigs with *M. bovis* bacilli killed by heat treatment or by antibodies of healthy patients or those affected by a disease other than tuberculosis.

These proteins are also characterized by the fact that they can be present in the culture medium.

According to a particular use of the invention, an antigenic determinant (epitope) originating from a biological agent other than *M. bovis* can also be grafted onto one of the proteins defined above.

Hybrid proteins are thus obtained of which the sequence includes the whole or part of the sequence of the proteins described above and a sequence corresponding to an antigenic determinant.

This determinant can be of various types and can in particular be a fragment of a protein or glycoprotein antigen, in order to obtain immunogenic compositions able to induce the synthesis of antibodies directed against these multiple antigenic determinants.

The use of bifunctional bridging agents such as glutaraldehyde or benzoquinone or N-bromosuccinimide, well known for their ability to interlink protein chains, or hydrazide allowing the linking of glycosyl residues with proteins, can be used for the formation of hybrid molecules. These hybrid molecules can be composed in part of a carrier molecule (45–47 kD complex), associated with one or several antigenic determinants or antigen fragments, for example diphtheria toxin or fragments thereof, tetanus toxin, the surface antigen of hepatitis B virus, poliomyelitis virus VP1 antigen.

The synthesis processes for hybrid molecules encompass the methods used in genetic engineering to construct DNA hybrids coding for the protein or peptide sequences required.

Such proteins can thus induce immunization against proteins or protein fragments corresponding to the antigenic determinants not present on the *M. bovis* proteins.

The invention also relates to the oligonucleotides, RNA or DNA, coding for the proteins defined above.

The present invention relates in addition to the protein fractions obtained from Mycobacterium cultures and in particular from *M. bovis* by a process including at least the following stages elimination of the bacteria from the culture medium by filtration, passage of the filtrate over a molecular sieve, and division of the eluate into fractions, and selection of the fractions by determination of their reactivity towards specific tuberculosis antibodies.

The fractions obtained by filtration over a molecular sieve can also be subjected to ion exchange chromatography and optionally to reversed phase chromatography.

The present invention also relates to the application of the proteins or the protein fractions or antibodies such as those defined above for the detection and monitoring of tuberculosis in particular in humans and bovines. Such detection can in particular be carried out by the Western Blot (immunoimprint) method or an immunoenzymological method (ELISA) or by a radioimmunological (RIA) method, by use of a measurement pack or kit, containing these proteins as well as in particular the buffers allowing the immunological reaction to be carried out and in addition substances allowing this to be revealed.

The present invention also relates to vaccines or drugs containing at least one protein, one protein fraction, or one antibody such as those defined above.

Vaccines containing nongrafted proteins can be used to immunize individuals against tuberculosis. The proteins carrying an antigenic determinant originating from a biological agent other than *M. bovis* can be used in the framework of immunization against other diseases.

As an indication, from 50 to 500 μg of protein can be used for an individual dose, or from $10^5$ to $10^6$ recombinant bacteria/individual by intradermic methods.

The present invention also relates to a pharmaceutical composition containing at least a pharmaceutically effective quantity of a protein, protein fraction or antibody, such as those defined above, in combination with pharmaceutically acceptable diluents or adjuvants.

In another respect, the present invention relates to the use of proteins, protein fractions or antibodies, such as those already defined above, for the manufacture of a drug for the treatment or prevention of tuberculosis.

The present invention is illustrated, without in any way being limited, by the following examples of implementation and with reference to the annexed drawings in which:

FIG. 1 shows the optical density (OD) profile at 220 and at 280 nanometers of the molecular filtration (Si 300) of the *M. bovis* culture medium.

FIG. 2 shows the optical density profile at 220 nanometers of the separation on ion exchange column (DEAE) of molecules originating from fraction 2 obtained during the above molecular filtration.

FIG. 3 shows the optical density profile at 220 nanometers of reversed phase column chromatography of fraction 1 resulting from the ion exchange chromatography.

FIGS. 4A and 4B are photographs of PVDF membranes in the presence respectively of a mixture of serums from guinea pigs immunized with dead (A) or live (B) bacilli.

FIG. 4C is an electrophoresis gel after coloration by Coomassie blue of the starting material (0) and of fractions obtained on the molecular sieve (1 to 6). Identical gels were transferred onto a PVDF membrane and revealed by serums from guinea pigs immunized by dead (4A) or live (4B) bacilli.

FIGS. 5A and 5B show PVDF membranes corresponding to a gel obtained by migration of fractions obtained on ion exchange columns (1 to 3) and of fraction 2 obtained by molecular sieve filtration, the said membrane being placed in the presence of antibodies of serums from guinea pigs immunized respectively with dead (A) or live (B) bacilli. FIG. 5C represents the original gel after the transfers of FIGS. 5A and 5B, colored by Coomassie blue.

FIGS. 6A and 6B show the imprint of gels on the membranes corresponding to the migration of fraction 1 obtained on ion exchange column (0) and the fractions obtained by reversed phase chromatography (1 to 5), placed in the presence of antibodies from serums from guinea pigs immunized respectively with dead (6A) and live (6B) bacilli. It should be noted that in fraction 1 of this purification stage, there is a contamination by the starting material due to too high a loading of the reversed phase chromatography column.

FIGS. 7A to 7L show the imprints of gels on membranes obtained through electrophoresis of starting material (0), fractions obtained by molecular sieve filtration (1 to 6) and placed in the presence of individual serums from patients affected by tuberculosis (7A to 7F) corresponding respectively to serum from patients (N°77, N°115, N°117, N°108, N°104, N°105) or by individual serums originating from patients suffering from Borrelia infection (7G to 7K) or yersiniosis (7L).

FIG. 8 shows the imprint of a gel on a PVDF membrane corresponding to the electrophoresis of fraction 5 obtained by reversed phase chromatography. This membrane was cut into approximately 3 mm strips, and each strip was placed in the presence of an individual serum (diluted 1/20) from a patient affected by tuberculosis (bands 1 to 14 corresponding respectively to patient N°77, 104, 105, 108, 115, 117, 124, 131, 134, 123, 3a, 2g, 2d, and 2a), or patients suffering from Borrelia infection (bands 15 to 19), leptospirosis (bands 20 to 22), yersiniosis (bands 23 and 24), or brucellosis (bands 25 to 27). The double "a" marks correspond to a common artefact in this technique.

FIG. 9 is a photograph of a two-dimensional gel colored with silver nitrate for proteins of 45–47 kD (fraction 5).

FIGS. 10, 11 and 12 represent some immunoblottings of crude antigens preparations of *M.bovis* AN5 (track 1), *M. avium* (track 2), *M.bovis* BCG (track 3), *M. tuberculosis* H37Rv (track 4), *M.kansaii* (track 5), *M. microti* (track 6), *M. smegmatis* (track 7), *M.xenopi* (track 8) respectively incubated with monoclonal antibodies of lines I-1483 (FIG. 10), $C_{13}$ (FIG. 11) and $A_5A_3$ (FIG. 12)

EXAMPLE 1

Antigen Purification Process

1) Preparation of Antigens

BCG cultures (strain 1173 P2) were made in flasks containing 130 ml of synthetic Sauton medium according to classical techniques (Gheorghiu et al. *Bull. Institut Pasteur* 1983, 81: 281–288). The culture medium was collected after 14 days at 37°, decanted and filtered (0.22 μm) at 4° C. The culture medium was placed on an Amicon (PM10) membrane under a nitrogen pressure of 2 bar and still at 4° C., washed intensively with retro-osmosed water containing 4% of butanol, then concentrated 10 to 20 times with respect to the initial volume. This concentrated culture medium, containing the molecules not excluded by the Amicon PM10 membrane, was freeze-dried, weighed, and stored in powder form at −20° C. The 12 g of starting material used for the purification scheme described below were obtained from 30 liters of culture medium. Purification scheme:

2) Gel Filtration

A Si300 preparative column, 3 μm of 50×750 mm (SERVA), was equilibrated by passage of a buffered saline solution ($Na_2HPO_4$ 50 rnM adjusted to pH 7.5 with $KH_2PO_4$) containing 4% of butanol; this solution had been previously filtered on a 0.22 μm membrane. The column flow was adjusted to 1.25 ml per min; the maximum pressure, set at 45 bar, was not reached.

The material to be injected onto the column was prepared at a concentration of 50 mg/ml in the buffer/butanol solution, ultracentrifuged at 40 000 g for 2 h, then filtered on a 0.22 μm membrane. 10 ml Samples were prepared and frozen at −20° C. Each 10 ml sample, filtered again after thawing and injected onto the column, contained approximately 500 mg of crude material. The optical density profiles at 280 and 220 nm are reported in FIG. 1 for a typical separation sequence. The six principal fractions selected based on the profile were concentrated at 4° C. and washed intensively on Amicon PM10 membrane with retro-osmosed water containing 4% of butanol. Each concentrated fraction was freeze-dried, weighed, and stored at −20° C. Fraction 2 of this stage contained the principal molecules recognized by the antibodies from guinea pigs immunized with live bacilli or by antibodies from tubercular patients. only this fraction was subjected to the following stage.

3) Ion Exchange Column

A DEAE-TSK 5PW preparative column of 21.5×150 mm (LKB) was equilibrated with a buffered saline solution ($Na_2HPO_4/NaH_2PO_4$ 10 mM, pH 7.5 and NaCl 10 mM) containing 4% of butanol. The maximum pressure was less than 30 bar for a flow of 6 ml/min. Only the NaCl concentration (1 M) was changed for the elution buffer. A linear gradient was applied according to the scheme shown in FIG. 2 after injection of a 4 ml sample containing a total of 100 mg of the above material. The principal fractions were collected according to the optical density profile at 220 nm. The fractions were concentrated and washed on a $PM_{10}$ (Amicon) membrane with retro-osmosed water containing 4% of butanol, then freeze-dried. After weighing, each fraction was stored at −20° C. Only fraction 1 of this, stage contained the majority of molecules recognized by the antibodies of guinea pigs immunized with live bacilli it was subjected to the following separation stage.

4) Reversed Phase Column

Figure 3:
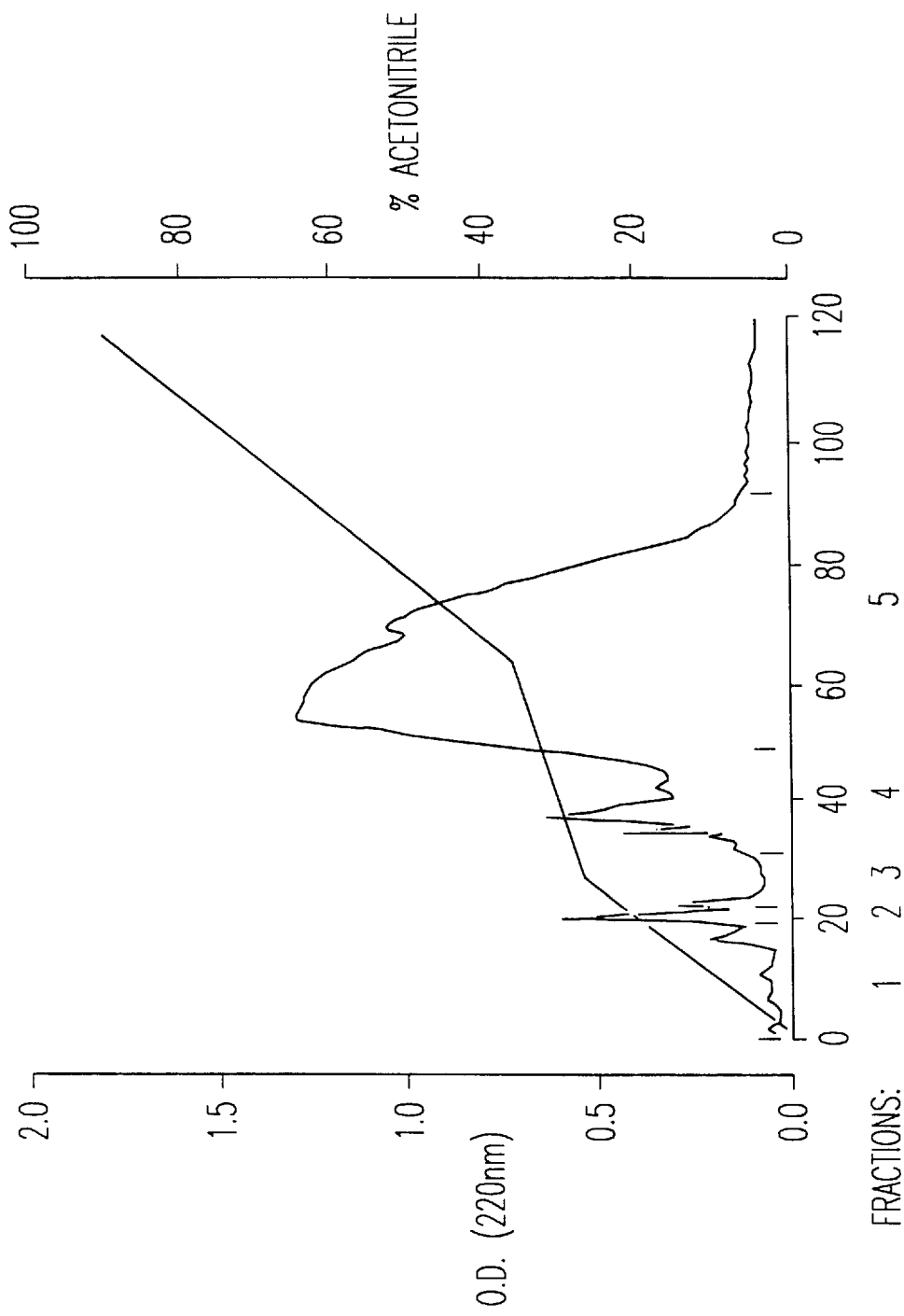

An RP 300 $C_8$ 10 Am column of 4.6×250 mm (Aquapore Brownlee Lab.) was equilibrated with an ammonium acetate ($NH_4COOCH_3$ 20 mM) buffer solution filtered at 0.22 μm with 2 ml/min flow under a maximum pressure of 115 bar. The elution buffer containing 90% of acetonitrile was used according to the profile shown in FIG. 3 after injection of a 10 mg sample in a 1 ml volume. The optical density profile at 220 nm allowed the separation of 5 principal fractions which were concentrated by vacuum evaporation at 40° C., then freeze-dried.

5) Immunodetection of Antiaens

10% Polyacrylamide, 0.1% SDS denaturing gels were prepared by the classical technique of Laemmli (Nature 1970, 277: 680–685). Samples containing between 10 and 2 μg of material, according to the purification stage, were applied in a buffer containing 5% of mercaptoethanol, 3% of SDS and a trace of Bromoplhenol blue in a volume of 10 ml in each gel track. After electrophoresis to the limit of migration of the blue the molecules present in the samples were transferred onto a PVDF (Millipore) sheet by applying a moderate electric field overnight (Harlow and Lane, Antibodies, A Laboratory Manual. Cold Spring Harbor Laboratory [eds] 1988).

A coloration of the PVDF sheet by a Coomassie blue solution for less than one minute, followed by a decoloration, permitted identification of the molecular weight markers, whose shape was outlined with a pencil mark. After total decoloration, the sheet was washed for 30 min at laboratory temperature with PBS+Triton X100 3%, then three times for 5 min with PBS alone. The sheet was then saturated with PBS containing 5% of skimmed milk powder for 1 h at 37° C., then washed three times with PBS+Tween 20 (0.2%).

An incubation was carried out with the antiserums (immunserums) diluted to ½oth in the PBS+Tween 20 (0.2%)+powdered milk 5% buffer during 1 h 30 min at 37° C. with periodic shaking. Three washings with PBS+Tween were then carried out before incubation with the anti-immunoglobulin antibodies labelled with alkaline phosphatase. The human anti-immunoglobulin antibodies and the guinea pig anti-immunoglobulin antibodies, labelled with phosphatase (Biosys) were used at a final dilution of ½500 in PBS+Tween 20 (0.2%)+milk (5%). After incubation for 1 h 30 min at 37° C., the PVDF sheets were washed three times in PBS+Tween, then incubated at laboratory temperature for 5 to 10 min, in the revealing buffer containing BCIP and NBT (Harlow and Lane, cited above). The reaction was stopped and after drying the sheets themselves were photographed.

6) Amino-acid Composition

An analysis for the overall amino-acid composition was carried out for each chromatographic fraction in the Institut Pasteur Organic Chemistry Department. A Beckmann LS 6300 analyzer was used.

The overall composition expressed in amino-acid frequency of the 45–47 kD proteins was as follows:

ASN/ASP: 10.6%; THR: 5.4%; SER: 5%; GLN/GLU: 6%; GLY: 7.4%; ALA: 19.2%; VAL: 5.8%; ILE: 2.3%; LEU: 4.7%; TYR: 2.2%; PHE: 2.29%; LYS: 2.9%; ARC: 2.5%; PRO: 21.9%.

EXAMPLE 2

Determination of the immunological specificity of the proteins and protein fractions.

A. Isolation of the Antigens Recognized by the Antibodies from Guinea Pigs Immunized with Live Bacilli Groups of 12 to 15 guinea pigs (Hartley females of 250 to 300 g at the beginning of the experiment) received either live mycobacteria ($2×10^7$ viable units of BCG in two intradermic injections in 0.1 ml of saline solution), or 2 mg of heat-killed (120° C., 30 min) mycobacteria from the same strain intramuscularly in 0.5 ml of a saline solution emulsion in incomplete Freund adjuvant (1/1). Serum samples from different groups of guinea pigs were taken 7 to 12 months after immunization, filtered (0.22 μm), then separated into small volumes which were frozen and stored at −20° C. Tests of several groups of antiserums were carried out (5 after immunization with live bacteria and 6 after immunization with killed bacteria). The results reported were obtained with a group of serums representative of each type of immunization; the differences between groups were minimal for the same immunization method.

1) Stage of Molecular Filtration on Si 300

The culture medium (washed, concentrated, and freeze-dried) constituting the starting material was injected in a sample volume of 10 ml containing 500 mg of material onto the Si 300 column. Fractions 1 to 6 were separated according to the profile shown in FIG. 1, collected for the 24 successive injections, then washed, concentrated, and freeze-dried. Table 1 gives the gross weight of each fraction after freeze-drying as well as the corresponding minimum weight of proteins, calculated from the concentrations of each classical amino acid determined by the amino-acid analysis of each fraction (Beckmann LS 6300 analyzer).

Each fraction (10 μg) was placed on an SDS gel track; then, after the electrophoresis sequence, transfer onto PVDF membrane and immunodetection, the fractions containing the major proteins reacting with the different serums were identified.

Figure 4:
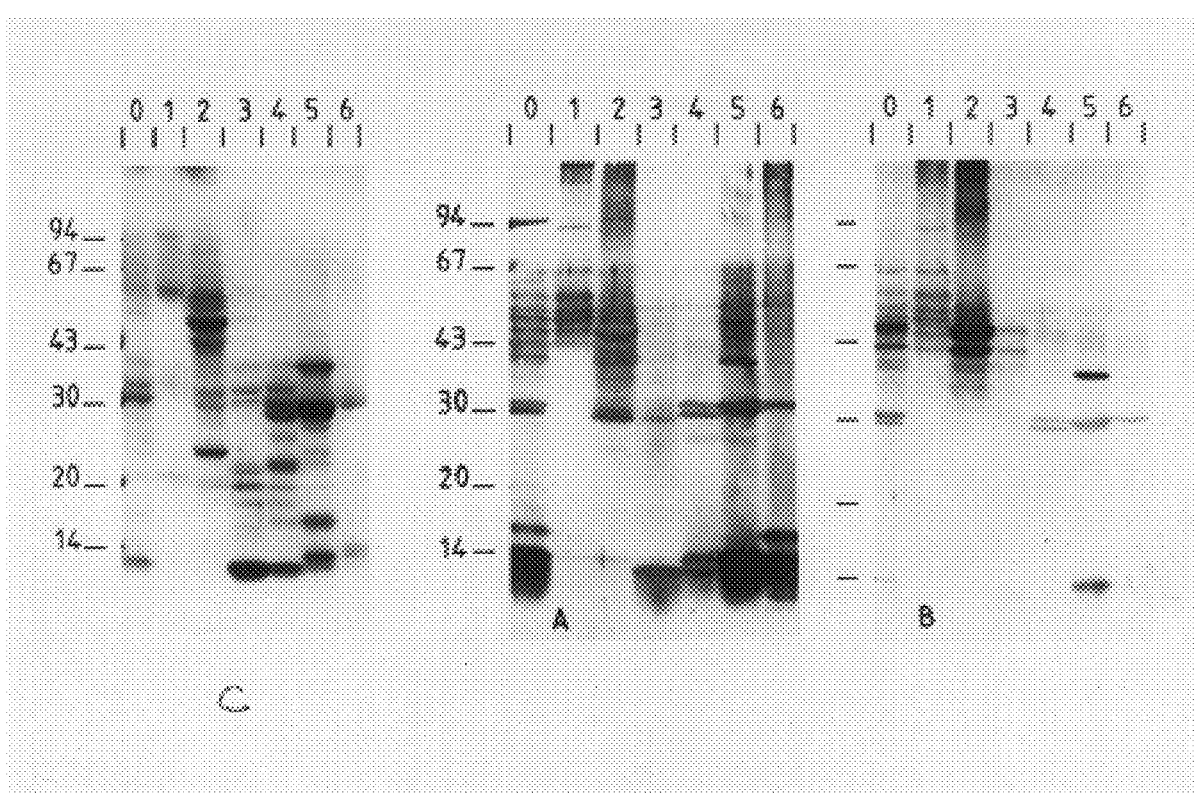

FIG. 4 shows a gel colored with Coomassie blue (FIG. 4C) and two immuno-imprints of identical gels revealed with serums from guinea pigs immunized with dead bacilli (4A) or with live bacilli (4B). Common antigens were recognized by both types of serum, such as the 30 kD antigens present in fractions 4, 5 and 6 and the 38 kD antigen in fraction 5. The antigens of molecular weights 10 to 16 kD in fractions 3, 4, 5 and 6 were recognized mainly by the antibodies from guinea pigs immunized with the dead bacilli. Two antigens of 45 and 47 kD present in fraction 2 were recognized mainly by the antibodies from animals immunized with the live bacilli. This fraction was selected for the second stage of purification.

2) Stage on Ion Exchange Column

Figure 2:
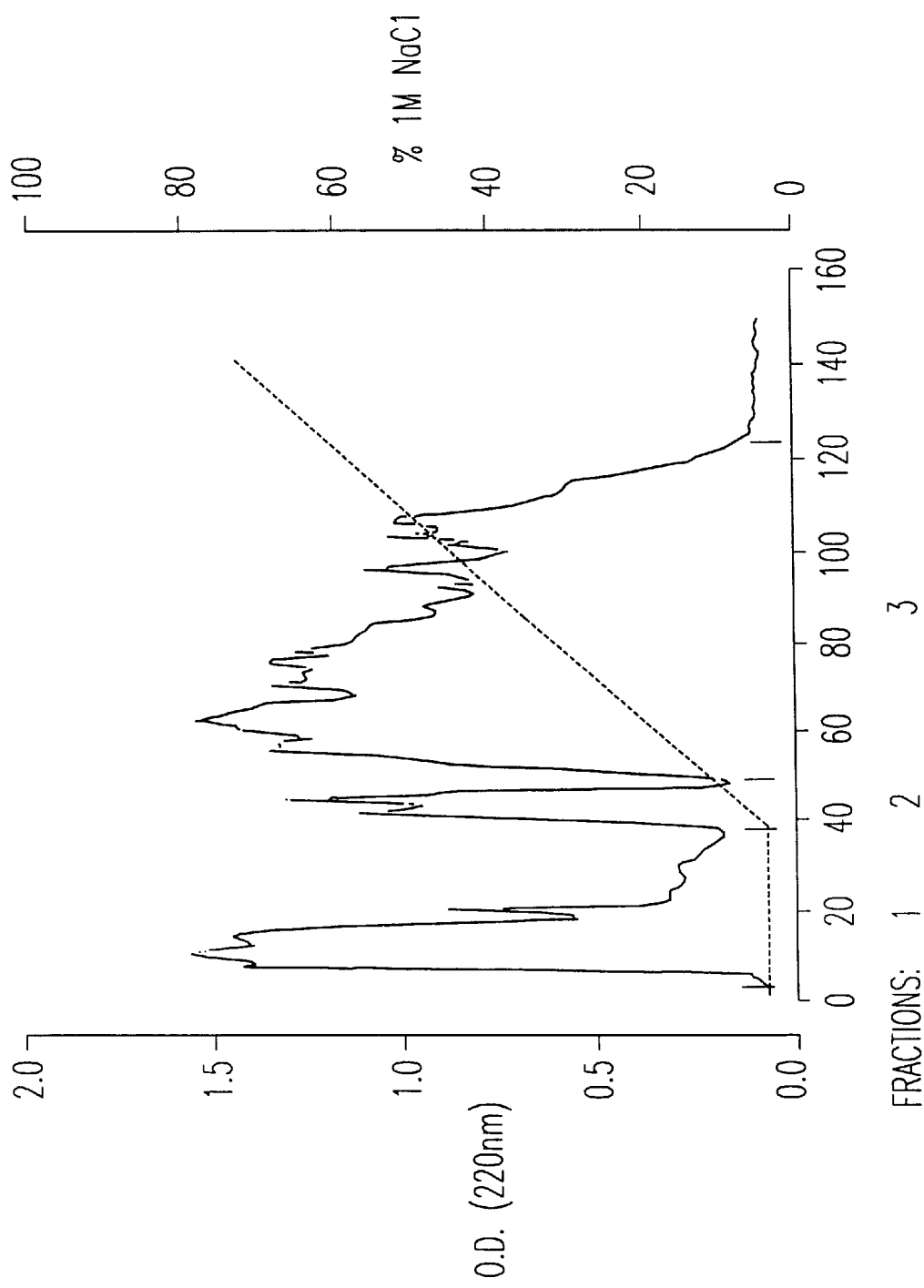

A 100 mg sample of the above fraction was loaded onto a DEAE-TSK preparative column and eluted with an NaCl gradient. The 220 nm profile of the molecules eluted defined three principal fractions (FIG. 2). After collection, each fraction obtained by the successive injections of material was washed, concentrated and freeze-dried (table 2).

Figure 5:
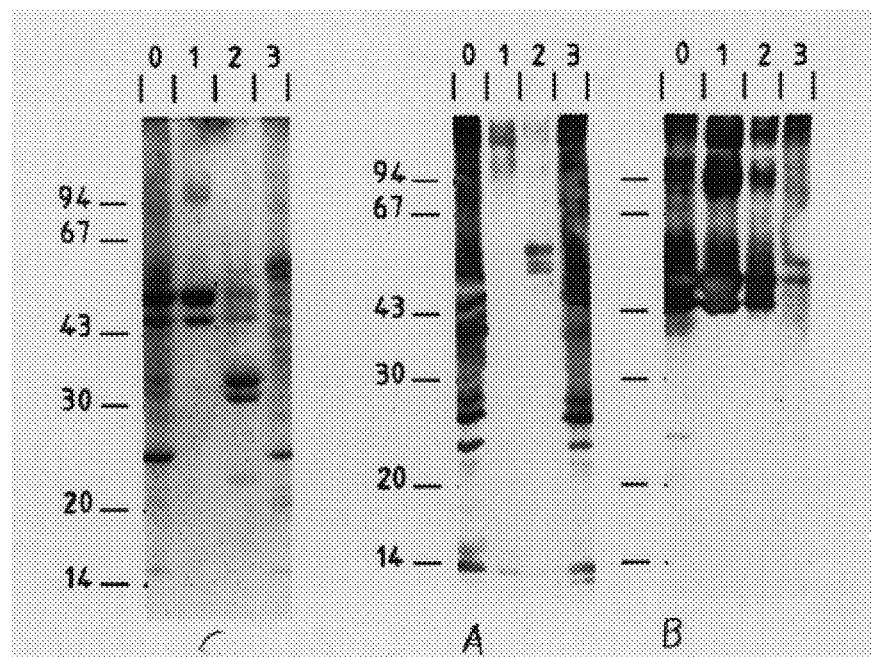

After electrophoresis on SDS gel of 5 μg of each of the above fractions, the immuno-imprints on PVDF sheets were revealed by the serums from guinea pigs immunized with dead or live bacilli (FIGS. 5A and 5B). The fraction 1-DEAE contained only a few antigens recognized by the antibodies from animals immunized with dead bacilli: two weak bands at approximately 10 and 14 kD, a weak band at 52 kD and a poorly defined shadow above 67 kD. On the other hand, this same fraction 1-DEAE contained a doublet at 45/47 kD strongly recognized by the antibodies from guinea pigs immunized with live bacilli, as well as a strong badly delineated spot between 67 and 94 kD. This fraction 1-DEAE was chosen for the following purification stage.

3) Stage on Reversed Phase Column

A 10 μm RP 300 column, equilibrated with the ammonium acetate buffer (20 mM), received a 1 ml sample containing a maximum of 5 to 10 mg of the above fraction 1-DEAE. Elution with an acetonitrile gradient of 0 to 90% according to the scheme of FIG. 3 allowed recovery of 5 principal fractions. These fractions were concentrated by vacuum evaporation at 40° to eliminate the majority of the acetonitrile, then freeze-dried. Table 3 shows the weights of each fraction.

Figure 6:
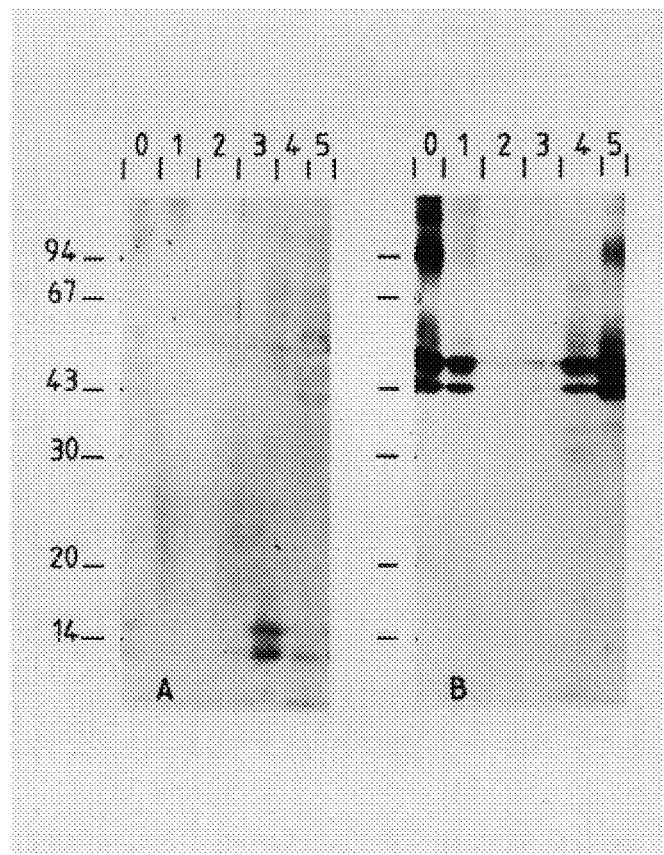

Fraction 4 which corresponded to an elution between 25 and 30% acetonitrile contained the 10 to 15 kD antigens recognized by the antibodies present in the serum of animals immunized with dead bacilli as well as a small amount of the 45/47 kD antigens recognized by the antibodies originating from the animals immunized with live bacilli. The following fraction 5 (30 to 50% acetonitrile gradient) contained the majority of the molecules recognized by the antibodies from the animals immunized with live bacilli and mainly these molecules (FIG. 6).

B) Tests of Antibodies Originating from Subjects Affected by Tuberculosis or Another Infectious Disease 1) Serums originating from 14 patients, showing either a recurrence of pulmonary tuberculosis (9 patients) or a first attack (5 patients), were used for the characterization of the principal antigens recognized by man during infection by *M. tuberculosis*.

| N° | Sex | Age | |
|---|---|---|---|
| 77 | M | 33 | 3rd attack, acute tuberculosis |
| 104 | F | 47 | 2nd attack, acute tuberculosis |
| 105 | M | 49 | 2nd attack, intermediate tuberculosis |
| 108 | M | 38 | 2nd attack, mild tuberculosis after previous acute after-effects |
| 115 | M | 64 | 2nd attack |
| 117 | M | 24 | 2nd attack |

-continued

| N° | Sex | Age | |
|---|---|---|---|
| 124 | M | 63 | 2nd attack |
| 131 | M | 64 | 2nd attack, tuberculosis currently very acute |
| 134 | M | 33 | 3rd attack, acute tuberculosis |
| 123 | F | 26 | 1st attack, intermediate tuberculosis |
| 3A | M | 45 | 1st attack, acute tuberculosis |
| 2G | F | 17 | 1st attack, intermediate tuberculosis |
| 2D | M | 27 | 1st attack, intermediate tuberculosis |
| 2A | M | 52 | 1st attack, acute tuberculosis |

2) Serums originating from 13 patients affected by an infectious disease with no known recent history of tuberculosis were used for the characterization of antigens not directly related to *M. tuberculosis* infection. The serum samples were taken to establish or confirm diagnoses of Borrelia infection (5 cases), leptospirosis (3 cases), yersiniosis (2 cases), or brucellosis (3 cases).

These serums from patients affected by tuberculosis or another infection were negative for the presence of anti-HIV and anti-Hbs (hepatitis B virus surface antigen) antibodies.

The fractions obtained after the first separation stage on Si 300 were subjected to electrophoresis, then to transfer onto PVDF membrane. Identical membranes were prepared and individually placed in the presence of a serum originating from a patient affected by tuberculosis or another infectious disease.

The results from 6 patients affected by tuberculosis and 6 patients affected by another infection showed that the 30 kD antigens present in fractions 4, 5 and 6 and the 35/38 kD antigens from fraction 5 were recognized by all the serums. In fraction 2 some antigens, in particular an antigen of 25 kD, were also recognized by all the serums. On the other hand, only the serums from patients affected by tuberculosis interacted strongly with the antigens located in the zone 45/47 kD (FIG. 7).

Figure 8:
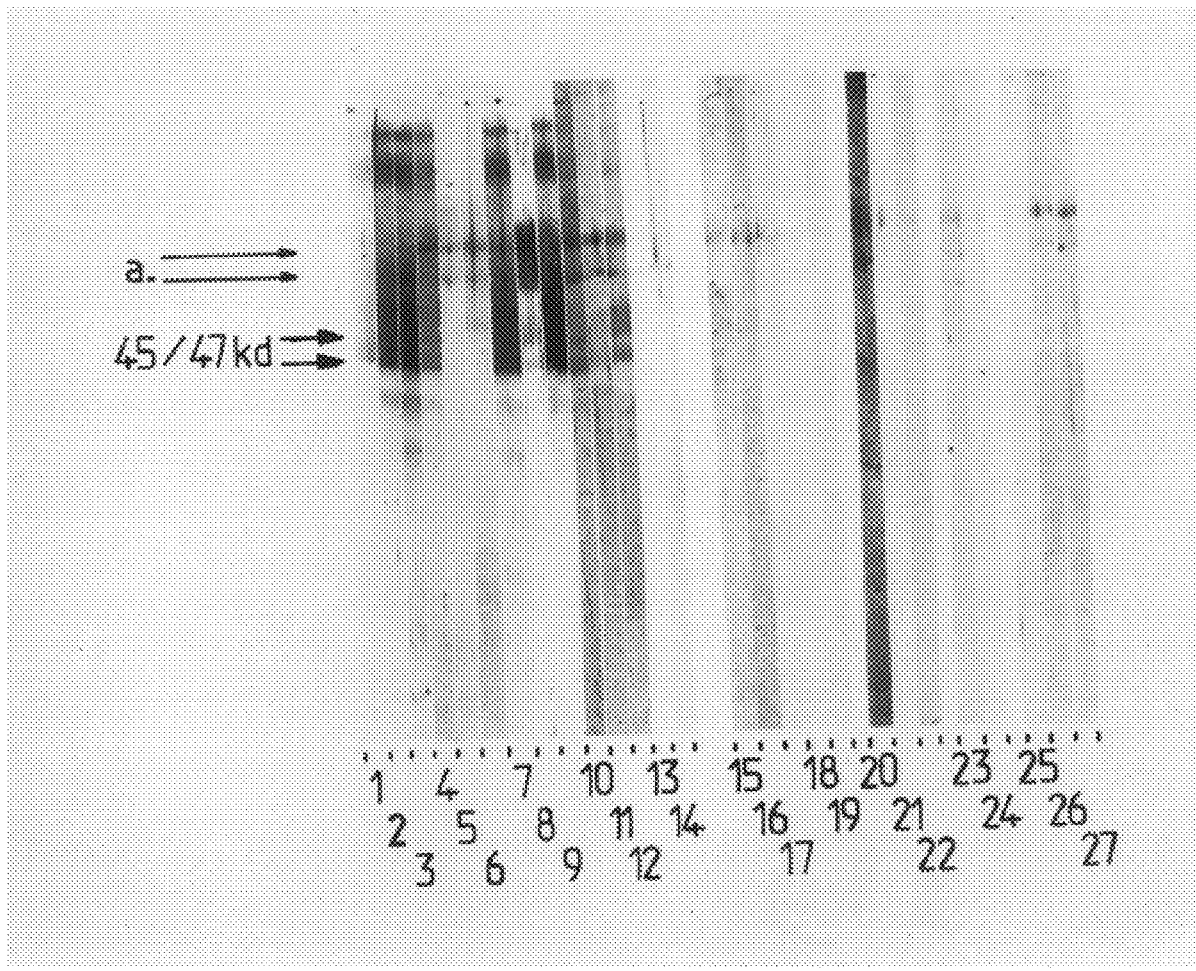

These 45/47 kD antigens, purified as described above, were placed on a very wide band of an SDS gel, then, after electrophoresis, they were transferred onto a PVDF membrane which was then cut into approximately 3 mm strips. Each strip was incubated in the presence of one of the patients' serums. As shown in FIG. 8, 12 of the 14 serums originating from patients affected by tuberculosis recognized the 45/47 kD antigens, while none of the serums from patients affected by other infections recognized these antigens.

C. Two-dimensional Electrophoresis of the Proteins in the 45–47 kD Group

Figure 9:
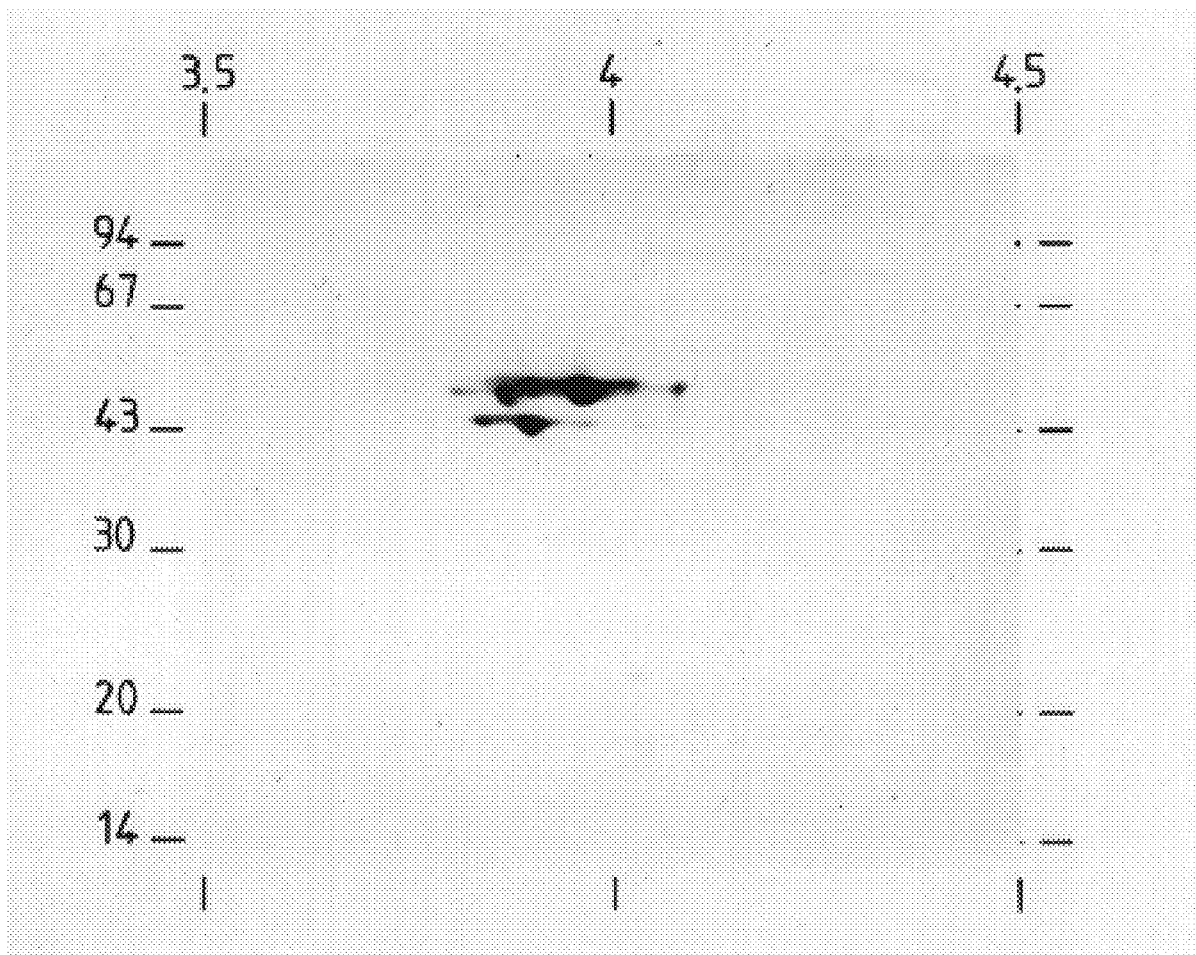

A two-dimensional electrophoresis of the proteins in the molecular weight group 45–47 kD was carried out, then the gel was colored with silver (FIG. 9).

The molecules were then transferred onto a PVDF sheet and then placed in the presence of antibodies from guinea pigs immunized with live bacilli or with antibodies from guinea pigs immunized with dead bacilli.

The results of the transfer showed that the molecules colored with silver were detected by the antibodies from guinea pigs immunized with live bacilli, while they were not recognized by antibodies from guinea pigs immunized with dead bacilli.

On the other hand, the 47 kD molecules of this complex were also recognized by the monoclonal antibodies from the hybridoma line deposited with the CNCM under the N° I.1081, and by the ones from the hybridoma line deposited with the CNCM under the N° I-1483.

EXAMPLE 3
Obtention of the Hybridoma Line I-1483

A classical protocol derived from the Milstein and Kohler's description and precisely described in the book of Methods in Enzymology n° 121 (1986) was used.

1) Obtention of the Hybridoma Line a) Immunization of Mice

Female Balb/C mice (8 to 10 weeks) received intraperitoneally (i.p.) 0.50 ml of a stable emulsion of incomplete Freund adjuvant and a phosphate buffered saline solution (PBS) (1/1 per volume) containing 30 µg of the purified 45/47 kDa antigen complex (PAC).

One month later the mice were injected i.p. with 0.50 ml of PBS containing 10 µg of the PAC, and thereafter three similar injections at 20 days interval. Test bleeds are collected 7 days after each booster immunization to monitor serum antibody levels.

The mice, checked 20 days after the last injection for the presence in their sera of the higher levels of antibodies were boosted by intravenous injection (0.50 ml) of PBS containing 5 µg of PAC 3 days before the collection of spleen cells.

b) Cell Lines

Myeloma cell line named X63 Ag8-653, provided by Dr Jean-Claude Mazié (Hybridolab, Institut Pasteur), was used for fusion. Its growing medium was RMPI 1640 supplemented with 10% fecal calf serum, 2 mM glutamine, 1 mM sodium pyruvate and 50 µg/ml of streptomycine.

c) Fusion Procedure and Selection of Hybrid Cells

Spleen cells ($4\times10^7$) prepared from immunized mice were fused with myeloma cells ($10^7$) in presence of polyethylene glycol 1500 (Boehringer-Mannheim) during 1 or 2 mn; the cell suspension was diluted around 40 times in growing medium and distributed $10^5$ myeloma cells per well of a 24-well Costar plate in 1 ml of H-AZA (hypoxanthine $5.10^{-5}$ M, azoserine $10^{-5}$ M) containing culture medium to obtain the correct selective condition for hybrid cells.

d) Selection of Antibody Secreting Hybrid Cells

After the progressive replacement of H-AZA medium by basal culture medium and the growth of hybridoma cells, the supernatant of each well was assayed for the presence of antibodies directed against the PAC, using an Elisa assay (see next paragraph).

e) Cloning Procedure by Limiting Dilution Assay

A procedure using two sequential cloning steps was used to clone hybridoma cells. In brief the cells of selected hydridoma cell lines present in the wells of a 24-well Costar plate were diluted in order to distribute one cell in each three wells of a 96-well plate. The growing cells were checked for their ability to produce the antibody directed against the PAC on the antibody titre present in the culture medium. A second identical cloning procedure was used for the cells present in the selected wells.

Elisa Assay

A classical Elisa assay was used to detect and to measure the concentration of the different antibodies. In brief the PAC was immobilized on the plastic surface (1 µg/ml in carbonate buffer, 50 µl per well) of a 96-well plate. After blocking the remaining sites with gelatin (0.25%) and extensive washing with PBS contained Tween 20 (0.2%), the antibody fluid to be assayed was appropriately, diluted in PBS/Tween/gelatin. The dilutions were left during 1 hour at 37° C., thereafter extensively washed with PBS/Tween and the specific mouse antibodies were detected using alkaline phosphatase labelled rabbit antibodies directed against mouse immunoglobulin (Biosys, 1/2500). The presence of alkaline phosphatase was revealed for 1 to 2 hours with para-nitrophenyl phosphate (Harlow E. & Lane D 1988, Antibodies: a laboratory manual. Cold Spring Harbor Laboratory, Cold Spring Harbor, N.Y.).

2) Isotyping of Monoclonal Antibodies

The immunoglobulin class and subclass of selected monoclonal hybridoma secreting cell clones was determined using the Elisa procedure described in the "Mouse Typer Sub-Isotyping Kit" (BIO-RAD).

3) Preparation of Crude Antigens

The excreted molecules present in the culture medium of *M. tuberculosis* (H37Rv), *M. bovis* (AN5), BCG (1137P2), *M. avium* (14.034.0002), *M. kansasii* (14.011.0001), *M. smegmatis* (mc2 155) and *M. xenopi* (14.035.0001) were collected and concentrated as previously described in Example 1 and in Infect. Immun. 1993, 61. In brief the mycobacterial strain was grown on Sauton medium during optimal time, i.e. the end of the exponential growing phase for the given strain. The culture medium was filtered through a gauze and a 0.22 µm-pore size filter (two successive 0.22 µm filtrations were performed for *M. tuberculosis* and *M. bovis* virulent strains). The collected media were intensively washed at 4° C. with de-ionized water containing butanol (4%) on a PM10 Amicon membrane and concentrated around 10-fold. The concentrated media containing molecules with molecular masses above 10 kDa were freeze-dried and stored at −20° C. The protein concentration of each sample was determined using the total amino-acid composition measured with a Beckmann apparatus on a weighed freeze-dried aliquot.

4) Immunoblotting

The antigens present in each crude antigen preparation (excreted molecules of *M. tuberculosis, M. bovis*, BCG, *M. avium, M. kansasii, M. smegmatis, M. xenophi*) were separated by SDS-polyacrylamide gel electrophoresis (PAGE) on 12.5% gels according to the method of Laemmli (Nature (London) 1970, 277: 680–685). Samples containing equivalent amount of proteins (3 µg) were loaded into the gel wells in 10 µl of buffer containing 5% 2-mercapto-ethanol, 3% SDS and a trace of bromophenol blue. After electrophoresis the molecules (antigens) present in each line were transferred on a polyvinylidene difluoride (PVDF) sheet (Millipore) by wet electrophoretic transfer (Towbin H. Stahelin T. and Gordon J. 1979, Proc. Natl. Acad. Sci. USA, 76: 4350–4354). The detection of immunoblots was performed as described previously (Harlow E. & Lane D. 1988 previously cited). In brief the PVDF sheet was rapidly stained with a solution of Coomassie blue in order to mark molecular weight markers with a pencil. After destaining the sheet was washed for 30 mn with PBS containing Triton X-100 (3%) at 25° C. and three more times with PBS alone for 5 mn each. The sheet was blocked with non fat dry milk (5%) in PBS for 1 hour at 37° C. and then extensively washed with PBS containing Tween 20 (0.2%).

The blocked and washed sheets were incubated in the presence of appropriate dilutions of the supernatent of the selected hydridoma cell clone or of the corresponding ascite fluids in PBS containing TWEEN 20 (0.2%) and non-fat dry milk (5%) for 1½ hours at 37° C. They were washed three times with PBS containing Tween 20 and incubated in the presence of an alkaline phosphatase conjugate directed against mouse immunoglobulin. These antibodies against mouse immunoglobulin (Biosys) were diluted (½500) in PBS-Tween 20 (0.2%)-non fat milk 5%. After inoculation for 1½ hours at 37° C. the PVDF sheets were washed three times in PBS-Tween 20 and were revealed for 5 to 10 mn with bromochlorin-dolylphosphate-nitroblue tetrazolium substrate.

5 -Characteristics of the Monoclonal Antibody Secreted by the Hybridoma Cell Clone I-1483

1) The monoclonal antibody was selected on its ability to bind on the proteins of the BCG 45/47 kDa antigen complex immobilized on a plastic surface in an Elisa.

2) The monoclonal antibody was selected on its ability to interact only on the proteins of the BCG 45/47 antigen complex in an immunoblotting assay performed as described previously. Only molecules present in the 45/47 kDa range were revealed in a crude BCG culture filtrate; the control purified molecules run on a parallel track were identically labelled in the very same range.

3) The monoclonal antibody revealed identical molecules in the culture filtrate of *M. tuberculosis (H37Rv)* and *M.bovis (AN5)*. The FIG. 10 corresponding to the monoclonal antibody produced by I-1483 shows the labelling of molecules present in the very same range in the tracks containing *M.tuberculosis* or *M.bovis* crude excreted molecules.

Figure 10:
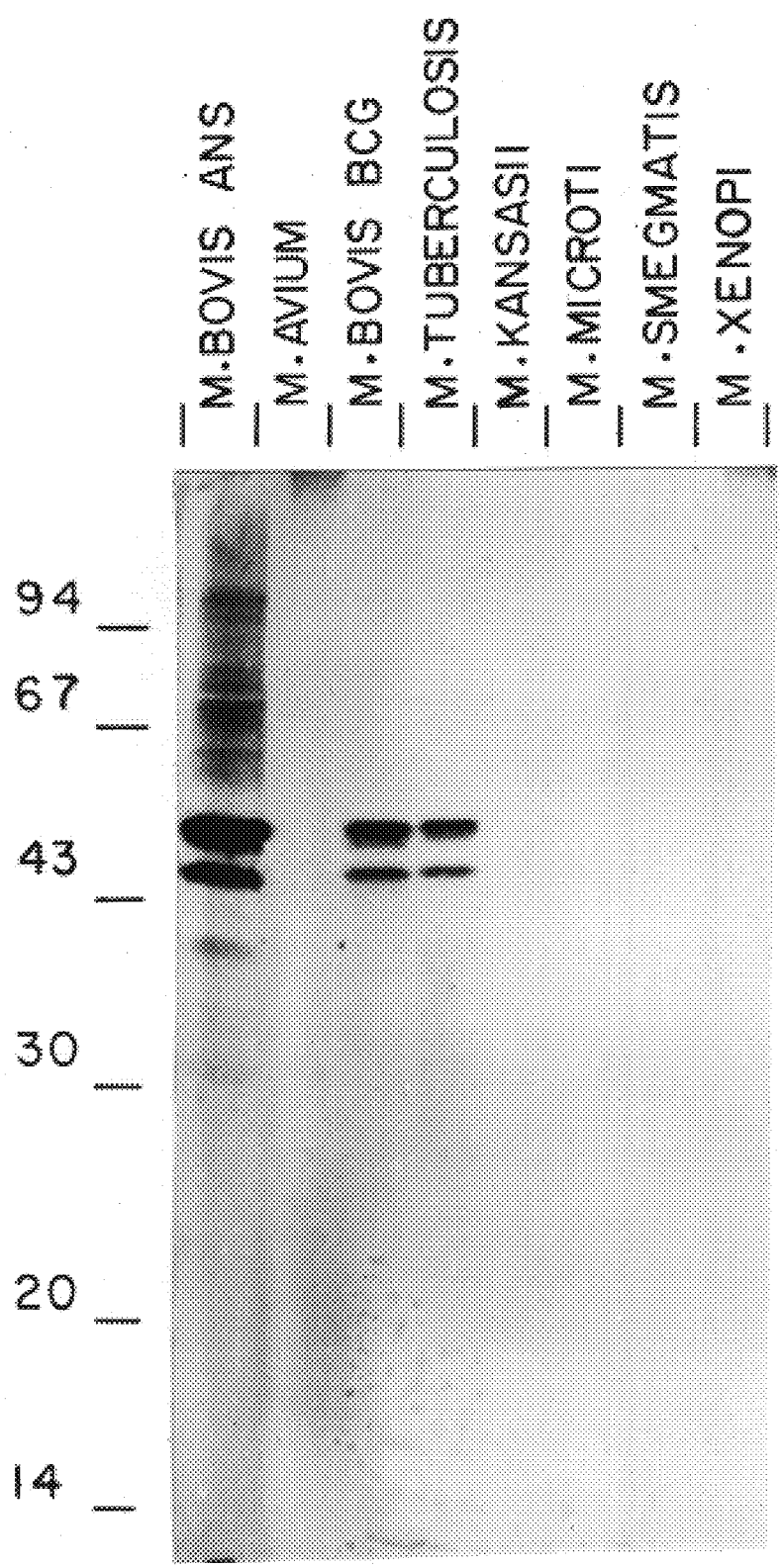

4) The monoclonal antibody did not reveal any band in the tracks of FIG. 10 containing *M. avium, M.kansasii, M.microti, M.smegmatis* or *M.zenopi* excreted molecules. In a parallel assay performed with these different crude culture filtrates but with a polyclonal rabbit antiserum directed against the PAC to reveal antigen, this polyclonal antiserum reacted with different discrete molecules.

Figure 11:
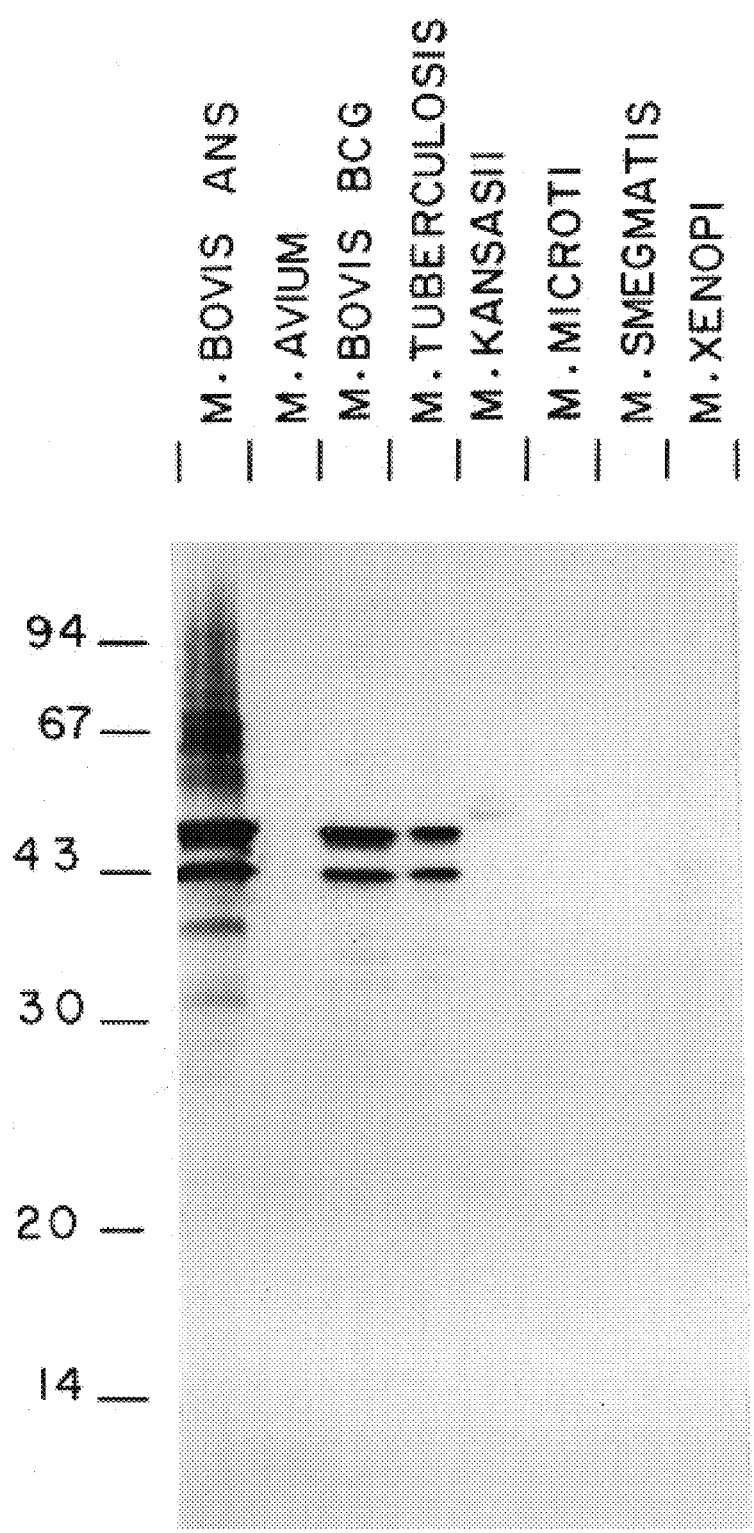
Figure 12:
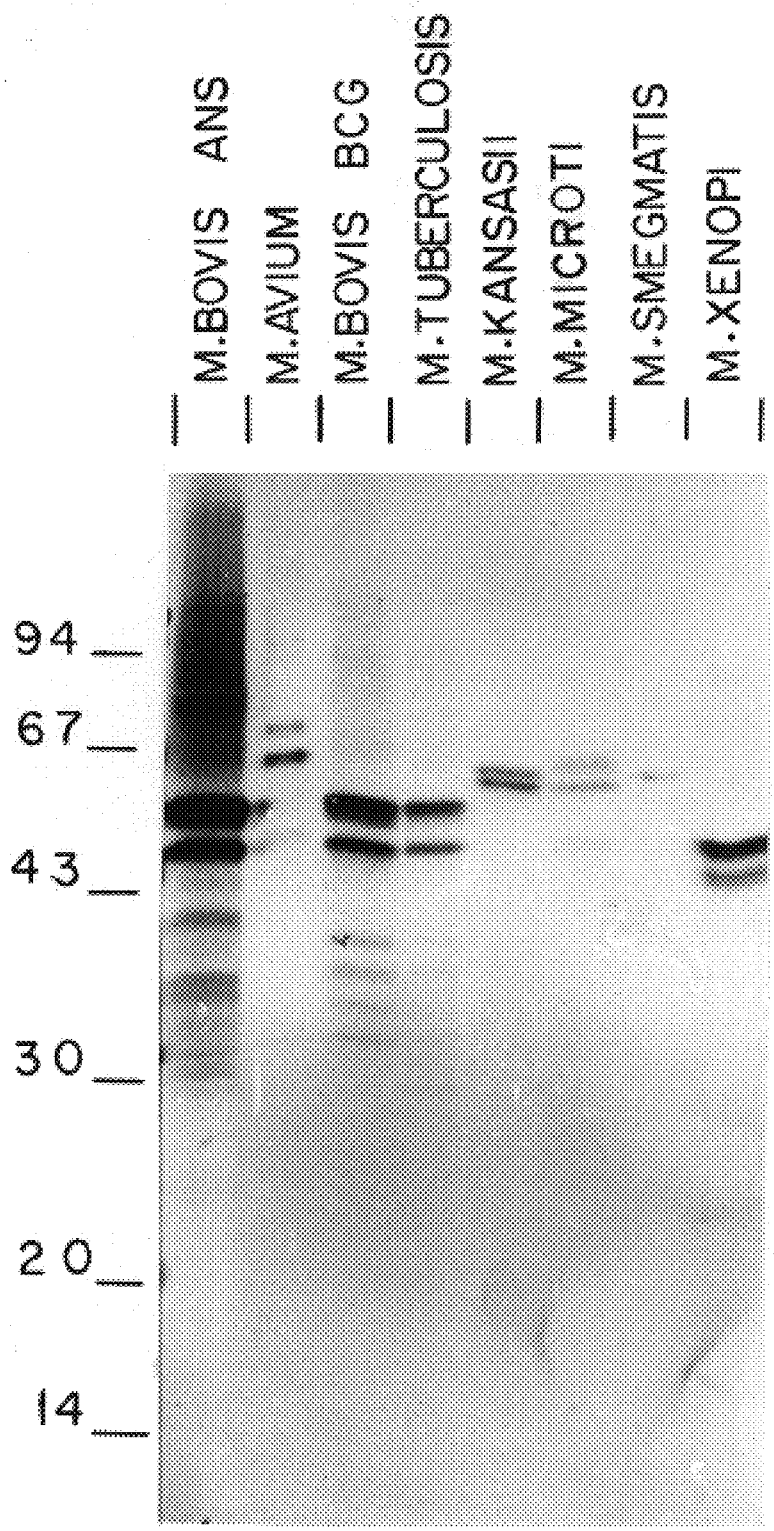

5) Similarly six other monoclonal antibodies were assayed for their ability to react with crossing antigens present in *M. avium, M. Lansasii, M. microti, M. smegmatis* or *M. xenopi* culture filtrates. The FIGS. 11 and 12 with monoclonal $C_{13}$ and $A_5A_3$ show that these monoclonal antibodies labelled the same molecules present at 70/80 kDa in *M. avium* culture filtrate, at 55/60 kDa in *M. kansasii* and *M. microti* culture filtrates, at 55/60 kDa in *M. smegmatis* culture filtrate or at 38/43 kDa in *M. xenopi* culture filtrate. These molecules faintly labelled by these monoclonal antibodies and also labelled by the rabbit polyclonal antiserum against the BCG 45/47 kDa antigen complex were never labelled by the herein described monoclonal antibody I-1483.

6) The present mouse monoclonal antibody I-1483 has been typed to be a IgG 2a immunoglobulin.

7) The cells of the selected clone were found to be able to grow in ascitic form in female Balb:c mice receiving pristane i.p. before the i.p. cell injection.

Conclusion

The results reported (FIG. 7) show that there exist in a Mycobacteria preparation,here in a culture medium,antigens recognized at the same time by serums from tubercular patients and by serums from patients affected by other infectious diseases.

On the other hand the antigens located in the 45/47 kD zone and present in fraction 2 of the Si300 column fractionation are only recognized by the serums from patients affected by tuberculosis and are not recognized by the serums from patients affected by another infection.

The 45/47 kD molecules, which have been purified on their antigenic capacity to react specifically with the serum from guinea pigs immunized with live bacilli, have isoelectric pH between 3.7 and 3.9, as determined on immobiline gel.

In the two-dimensional gel the 47 kD band was resolved into two principal spots after coloration with silver nitrate at pHi values of 3.7 and 3.9, and the band at 45 kD into a principal spot at pHi 3.7. Medium intensity spots were also displayed by this method, and were part of the 45/47 kD complex. The different molecules thus detected in the two-dimensional gel were all recognized by the serum from animals immunized with live bacilli.

No other discernable molecules existed after coloration of the gel with Coomassie blue or silver.

Similarly, after transfer onto PVDF membrane then immunodetection with serums from guinea pigs immunized with heat-killed bacilli, no visible spot existed either in the 45/47 antigen zone, nor elsewhere.

Serums from rabbits immunized against a crude preparation of mycobacterial antigens only detected the 45/47 kD molecules, thus demonstrating their purity according to these biochemical and immunochemical criteria.

A monoclonal antibody prepared from the mouse recognized the different 47 kD molecules in an immunodetection test after transfer of the molecules present on a two-dimensional gel onto a PVDF membrane.

None of the immunological reagents which were tested (guinea pig serums after different periods of immunization with live bacteria, serums from patients affected by tuberculosis) could dissociate the molecules of the 45/47 kD complex on the basis of antigenic activity.

The N terminal sequence determinations of proteins of 47 and 45 kDa were identical, which is also in favor of a close relationship between them.

TABLE I

Total weight of each Si 300 fraction and evaluation of the corresponding protein weight.

| Fraction | Gross weight (mg) | % amino acids | Protein weight (mg) |
| --- | --- | --- | --- |
| Fr 1 | 578 | 15 | 86 |
| Fr 2 | 230 | 64 | 147 |
| Fr 3 | 580 | 53 | 308 |
| Fr 4 | 460 | 51 | 236 |
| Fr 5 | 62 | 67 | 42 |
| Fr 6 | 370 | 44 | 161 |
| Total | 2280 | | 960 |

Table I legend
From 12 g of raw material, containing a minimum of 2.2 g of proteins, 6 fractions were obtained by molecular filtration on Si 300. The calculation of minimum weight corresponding to proteins was made from the results of the overall amino-acid composition.
The total yields were 19% for the gross weight yield and 44% for the calculated protein yield.

TABLE 2

Total weight of each DEAE fraction and evaluation of the weight corresponding to proteins.

| Fraction | Gross weight (mg) | % amino acids | Protein weight (mg) |
| --- | --- | --- | --- |
| Fr 1 | 58.4 | 68 | 39.7 |
| Fr 2 | 8.4 | 32 | 2.7 |
| Fr 3 | 78.5 | 86 | 68.0 |
| Total | 145.3 | | |

Table 2 legend:
The above Si 300 fraction 2 was loaded onto a DEAE-TSK preparative column. The fraction not retained by the column constituted fraction 1-DEAE, fractions 2 and 3 corresponded to the elution by increasing ionic strength (between 10 mM and 600 mM NaCl).
The yields were 63% for the gross weight yield and 75% for the yield calculated for the proteins after analysis of the amino-acid composition of each fraction.

TABLE 3

Total weight of each RP 300 reversed phase fraction and evaluation of the corresponding protein weight.

| Fraction | Gross weight (mg) | % amino acids | Protein weight (mg) |
|---|---|---|---|
| Fr 1 | 15.0 | 13 | 2.0 |
| Fr 2 | 2.3 | 18 | 0.4 |
| Fr 3 | 1.5 | 13 | 0.2 |
| Fr 4 | 4.1 | 65 | 2.7 |
| Fr 5 | 29.9 | 77 | 23.0 |
| Total | 52.8 | | 26.3 |

Table 3 legend:
The above fraction 1-DEAE was loaded onto a RP 300 (Aquapore) column, then eluted with an acetonitrile gradient from 0 to 90% according to the scheme shown in FIG. 5.

7. The protein of claim 4, wherein said protein has an $NH_2$ terminal with the following sequence (SEQ ID NO:1):

```
ALA-PRO-GLU-PRO-ALA-PRO-PRO-VAL-PRO-PRO-ALA-ALA-
1   2   3   4   5   6   7   8   9  10  11  12

ALA-ALA-PRO PRO ALA
13  14  15  16  17.
```

8. The protein of claim 2, wherein said protein has an amino-acid composition expressed by frequency for PRO of approximately 21.9%, for ASN/ASP approximately 10.6%, for THR approximately 5.4%, for SER approximately 5%, for GLN/GLU approximately 6%, for GLY approximately 7.4%, for ALA approximately 19.2%, for VAL approximately 5.8%, for ILE approximately 2.3%, for LEU approximately 4.7%, for TYR approximately 2.2%, for PHE approximately 2.2%, for LYS approximately 2.9% and/or for ARG approximately 2.5%.

9. The protein of claim 2, wherein said protein is present in a culture medium of *Mycobacterium bacilli*.

10. A method for detecting or monitoring the development of tuberculosis in man or cattle, comprising assaying a biological sample from said man or cattle for antibodies which bind specifically to a protein isolated from Mycobacterium and having a molecular weight in the presence of SDS between about 44.5 and 47.5 kD, wherein said protein is recognized by antibodies obtained by immunization with live *Mycobacterium bovis* bacilli, by the antibodies from tubercular patients and by an antibody secreted by a hybridoma deposited under No. I-1081 at the CNCM or a hybridoma line deposited under No. I-1483 at the CNCM, and is not recognized by the antibodies obtained by immunization with heat-killed *Mycobacterium bovis* bacilli or by antibodies from healthy patients or patients affected by a disease other than tuberculosis;

detecting the presence of said antibodies in the biological sample; and correlating the presence of said antibodies in the biological sample with the development of tuberculosis.

We claim:

1. A protein isolated from Mycobacterium and having a molecular weight in the presence of SDS of between about 44.5 and 47.5 kD, wherein said protein is recognized by antibodies obtained by immunization with live *Mycobacterium bovis* bacilli, by the antibodies from tubercular patients and by an antibody secreted by a hybridoma deposited under No. I-1081 at the CNCM or a hybridoma line deposited under No. I-1483 at the CNCM, and is not recognized by the antibodies obtained by immunization with heat-killed *Mycobacterium bovis* bacilli or by antibodies from healthy patients or patients affected by a disease other than tuberculosis.

2. The protein of claim 1, wherein said protein is isolated from *Mycobacterium bovis*.

3. The protein of claim 2, wherein said protein has a molecular weight of approximately 45 kD.

4. The protein of claim 2, wherein said protein has a molecular weight of approximately 47 kD.

5. The protein of claim 2, having a pHi of approximately 3.7.

6. The protein of claim 2, having a pHi of approximately 3.9.

11. A process for the detection and monitoring of the development of tuberculosis in man and in cattle comprising the steps of:

a) bringing a protein according to claim 1 into contact with a serum sample of a patient under conditions sufficient to obtain a complex between said protein and any antibody present is said serum sample; and b) detecting said complex.

* * * * *

UNITED STATES PATENT AND TRADEMARK OFFICE
CERTIFICATE OF CORRECTION

PATENT NO. : 6,060,259

DATED : May 9, 2000

INVENTOR(S): Cynthia HORN, et al.

It is certified that an error appears in the above-identified patent and that said Letters Patent is hereby corrected as shown below:

On the Title page, Item [19] and [75], the order of the Inventors' names is listed incorrectly. Item [19] and [75] should read as follows:

---      [19]    Horn et al.     ---

---      [75]    Inventors:     Cynthia Horn; Pascale Pescher, both of Paris; Gilles Marchal, Ivry; Felix Romain, Fontenay-Les-Briis; all of France     ---

On the Title page, Item [63], and Column 1, the Related U.S. Application Data is incomplete. Item [63] and Column 1 should read as follows:

---      Related U.S. Application Data

[63]    Continuation-in-part of application No. 08/142,483, filed as International Application No. PCT/FR92/00508, Jun. 5, 1992     ---

Signed and Sealed this

Eighth Day of May, 2001

*Attest:*

NICHOLAS P. GODICI

*Attesting Officer*     Acting Director of the United States Patent and Trademark Office

SEQUENCE LISTING

```
(1) GENERAL INFORMATION:

(iii) NUMBER OF SEQUENCES: 1

(2) INFORMATION FOR SEQ ID NO:1:

(i) SEQUENCE CHARACTERISTICS:
          (A) LENGTH: 17 amino acids
          (B) TYPE: amino acid
          (C) STRANDEDNESS: Not Relevant
          (D) TOPOLOGY: linear (ii) MOLECULE TYPE: peptide (xi) SEQUENCE DESCRIPTION: SEQ ID NO:1:

Ala Pro Glu Pro Ala Pro Pro Val Pro Pro Ala Ala Ala Ala Pro Pro
1               5                   10                  15

Ala
```